United States Patent [19]
O'Connor et al.

[11] Patent Number: 4,896,010
[45] Date of Patent: Jan. 23, 1990

[54] MICROWAVE DRYING & SANITIZING OF FABRIC

[75] Inventors: Mary E. O'Connor; Michel J. Cloutier; Robert D. Strattan; James R. Sorem, Jr., all of Tulsa, Okla.

[73] Assignee: Micro Dry, Incorporated, Tulsa, Okla.

[21] Appl. No.: 284,704

[22] Filed: Dec. 15, 1988

Related U.S. Application Data

[62] Division of Ser. No. 129,161, Dec. 7, 1987, Pat. No. 4,829,679.

[51] Int. Cl.$^4$ .............................................. H05B 6/64
[52] U.S. Cl. ..................... 219/10.55 M; 219/10.55 R; 34/1; 422/21
[58] Field of Search ................ 219/10.55 R, 10.55 A, 219/10.55 M; 34/1; 422/21–23, 121, 186

[56] References Cited

U.S. PATENT DOCUMENTS

| 3,605,272 | 9/1971 | Boucher | 34/1 |
| 3,854,219 | 12/1974 | Staats | 219/10.55 A X |
| 3,858,329 | 1/1975 | Koide et al. | 34/1 |
| 4,365,422 | 12/1982 | Kawaguchi | 219/10.55 M X |
| 4,405,850 | 9/1983 | Edgar | 219/10.55 A |
| 4,471,192 | 9/1984 | Awata et al. | 219/10.55 A |
| 4,771,156 | 9/1988 | Strattan et al. | 219/10.55 M |
| 4,795,871 | 1/1989 | Strattan et al. | 219/10.55 M |

Primary Examiner—Philip H. Leung
Attorney, Agent, or Firm—Robert S. Salzman

[57] ABSTRACT

The invention features a sanitization method and apparatus utilizing multiple microwave sources. Bacteria are killed by the combination of microwave heated water vapor, which is allowed to accumulate within the sealed chamber, and the microwave field effect acting in synergy with the accumulated water vapor.

1 Claim, 1 Drawing Sheet

MICROWAVE DRYING & SANITIZING OF FABRIC

This is a divisional application of Ser. No. 129,161; filed: Dec. 7, 1987, U.S. Pat. No. 4,829,679.

FIELD OF THE INVENTION

The invention relates to a microwave clothes and fabric drying apparatus and method, and more particularly to a method and apparatus for both drying and sanitizing the fabric during the drying cycle.

RELATED APPLICATION

This application is related to the prior filed U.S. patent application, Ser. No. 092,621; filed: Sept. 3, 1987. Priority is claimed for all common subject matter, which is meant to be incorporated herein by way of reference.

BACKGROUND OF THE INVENTION

As far back as twenty years ago, suggestion was made that clothes could be sterilized by irradiation with microwaves. Such suggestion can be found in U.S. Pat. No. 3,605,272; issued: Sept. 20, 1971.

However, despite this disclosure, very little is definitely known about killing bacteria using microwave energy.

A careful survey of scientific articles and journals indicated that parameters and mechanisms by which bacteria can be killed by microwaves is not well understood. In fact, there are published articles that even suggest that bacteria growth can be enhanced by microwave irradiation.

On this note, the present inventive research, set the task of developing a verifiable method for sanitizing clothes and fabrics heated and dried by microwaves.

Using an apparatus similar to that described and shown in U.S. patent application, Ser. No. 092,621, clothes and fabrics were heated and dried by multiple magnetron units, each producing approximately 700 Watts, and operating at approximately 2,450 MHz. The multiple microwave sources were cross-polarized. The tested fabric articles respectively contained different strains of bacteria, such as: E. Coli; Salmonella; Shigella, etc.

It was discovered that bacteria could be killed using microwaves, and that the effective mechanism by which this was accomplished was not entirely heat dependent. In other words, the microwave field effect itself was a contributing mechanism by which decontamination was accomplished.

Thus, heating and drying by microwaves provides a sanitizing advantage that ordinary heating and drying techniques cannot accomplish.

Furthermore, it was also discovered that the airflow necessary for carrying away evaporated moisture, could seriously complicate the sanitizing process by introducing air-borne contaminants.

It was further discovered during the testing, that the fabrics could be heated by microwaves without removing the moisture from the drying chamber. Heated in this way, it was observed that an enhanced sanitizing effect was obtained. Bacteria were more easily killed by the combination of the microwave field effect and the accumulated and heated moist air which was now trapped within the heating chamber.

However, the microwave field effect in combination with the confined, heated water vapor (steam) proves a synergy in sanitizing fabric heretofore unknown.

Sanitizing fabric by microwave energy is now conclusively a reality.

BRIEF SUMMARY OF THE INVENTION

The invention features a method and apparatus whereby moise fabrics that are heated and dried by microwaves can be simultaneously sanitized. The method establishes at least one sanitization sub-cycle during a portion or portions of the microwave heating cycle.

The sanitization sub-cycle comprises the step of accumulating and heating the vaporized moisture effluent emanating from the microwave irradiated fabrics during a portion of the microwave heating cycle. The trapped moisture is confined within a "heating zone", which for the purposes of definition shall mean either a heating and drying chamber as used in a stationary, commercial system, or a heated work station adjacent a conveyor, as would be utilized in an industrial, bulk, or continuous system.

When the vaporized moisture (steam) is allowed to remain and be further heated within the "heating zone", the microwave field effect in combination with the heated vaporized moisture causes a sanitizing of the fabrics.

The portion of the microwave heating cycle in which the sanitization sub-cycle is accomplished is generally at the beginning thereof; after which, the fabric is further heated with application of a conventional airflow to complete the drying process.

It is also contemplated by this invention that there can be established a second, or additional sanitization sub-cycle at an end portion of the microwave heating cycle, in order to kill any air-borne contaminants introduced by the subsequent drying airflow.

It is also contemplated that the drying airflow can be adequately filtered to prevent introduction of air-borne contaminants. In such circumstance, the second sanitization sub-cycle would not be necessary.

In the sanitization of other articles in addition to fabrics and clothing, such as: plastics, instruments, and sealed non-perishables, moisture may be introduced to the heating zone.

The sanitization sub-cycle does not increase the drying time for the fabrics, since it is itself a fractional cycle of the heating step. The sanitization sub-cycle will comprise up to 50% of the microwave heating cycle.

The moise fabrics are tumbled within a rotatable microwave-permeable drum which is disposed within the "heating zone". The microwaves penetrate the tumbling drum, causing the moisture within the fabrics to evaporate.

In continuous systems featuring a conveyor belt, the clothes may be agitated by rotating vanes as they travel through the "heating zone". There may be several heat work stations for the above purpose.

It is an object of this invention to provide an improved microwave drying system wherein fabrics and other articles can be sanitized as they are dried.

It is another object of this invention to provide a sanitization method and apparatus which utilizes both microwave field effect and heated moisture to killed bacteria.

These and other objects of the invention will be better understood and will become more apparent with reference to the following detailed description considered in conjunction with the accompanying drawings.

DETAILED DESCRIPTION OF THE INVENTION

Generally speaking, the invention pertains to a method and apparatus for heating, drying, and sanitizing moise fabric articles by microwave energy. The vaporized moisture driven off by the microwave irradiation, is accumulated within the heating zone. The accumulated moisture is itself heated during the irradiating process. This heated vapor in combination with the microwave field effect kills bacteria entrained within the fabric articles in a more facile manner heretofore unknown.

Figure 1:
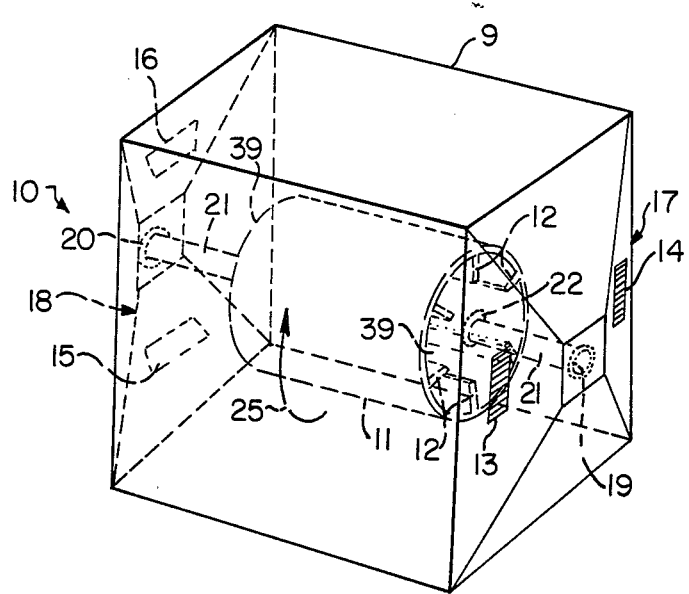
FIG. 1 is a perspective schematic view of an apparatus used for the drying and sanitizing of fabrics in accordance with the teachings of this invention.

Now referring to FIG. 1, a moist fabric microwave heating and drying apparatus 10 comprising heating chamber 9, is illustrated in schematic view. The airflow system shown in the sectional view of FIG. 2 has been deleted from FIG. 1 for the sake of brevity, but will be understood to be part of the entire apparatus 10 therein.

For purposes of clarity and brevity, the same elements will carry the same designation throughout the figures.

Moist fabrics (not shown) are loaded into a removable, rotatable tumbling drum 11, which has internal vanes 12 for tumbling the moist fabric as the drum rotates (arrow 25).

The tumbling drum 11 is microwave permeable, being made of a plastic such as Lexan, so that moist fabrics disposed within the drum can be irradiated. Microwaves are directed at drum 11 from magnetron fed waveguides 13, 14, 15 and 16, respectively disposed about heating chamber 9, as illustrated.

The chamber 9 can be of a generally rectangular shape with two side walls 17 and 18, respectively configured with pyrimidal-shaped quarter panels.

Figure 2:
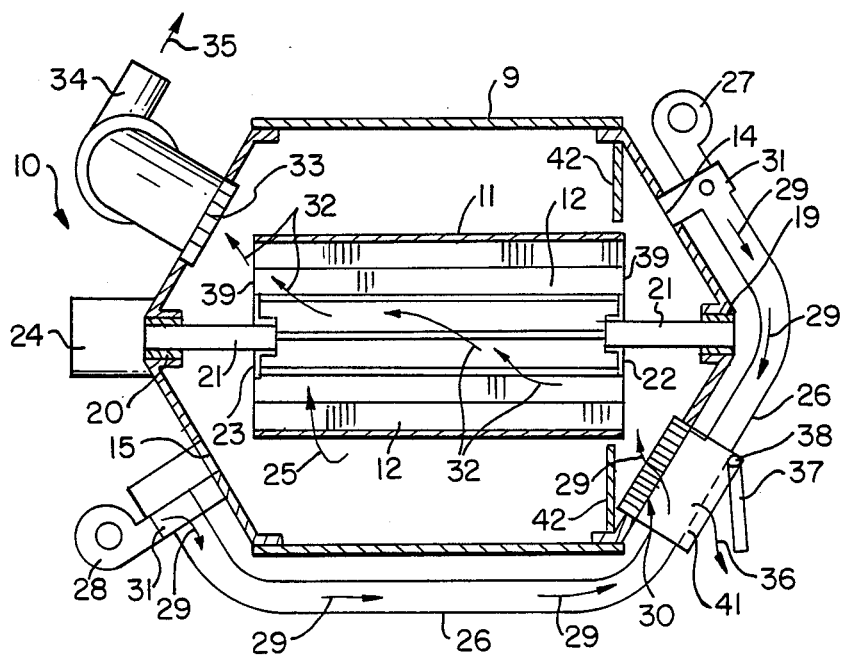
FIG. 2 is a schematic sectional view of the apparatus shown in FIG. 1, depicting in more detail the airflow system used for the drying and sanitization of the fabrics.

At the apex of walls 17 and 18, are respective internal bearings 19 and 20, for rotatively supporting drum shaft 21 which is fixedly attached to respective distal ends 22 and 23 of drum 11 (FIG. 2).

A motor 24 rotatively drives the drum shaft 21, thus causing drum 11 to rotate (arrow 25) within end bearings 19 and 20.

The end walls 17 and 18 are each pyrimidal-shaped so that the respective magnetron waveguides 13, 14, 15 and 16 project the microwaves inwardly toward the center of drum 11. Waveguides 13 and 14 are vertically oriented, while waveguides 15 and 16 are horizontally oriented, such that the microwaves projected from chamber walls 17 and 18 are cross-polarized with respect to each other.

The airflow system of this invention is illustrated in FIG. 2. There are two air ducts 26, only one of which is shown in the sectional view of FIG. 2. Each duct 26 has two squirrel-cage blowers 27 and 28, respectively disposed therein as shown. Each of the blowers 27 and 28 feeds air (arrows 29) through duct 26 towards, and into, a common chamber inlet 30. Each blower 27 and 28 cools a magnetron 31 disposed adjacent its respective waveguide. There are a total of four magnetrons 31. Each magnetron 31 produces approximately 700 watts of 2,450 MHz. There are two magnetrons 31 in each air duct 26.

During the drying portion of the microwave heating cycle, air enters inlet 30 of chamber 9 from the two air ducts 26, and is directed with aid of a microwave permeable deflector 42 across the heating chamber 9 (arrows 32) towards chamber outlet 33. The airflow 32 passes through tumbler drum 11 as it rotates and tumbles the fabric (arrow 25).

Evaporated moisture resulting from the microwave heating of the moist fabric is then carried away by airflow 32, and exists chamber 9 at outlet 33. An exhaust duct 34 and fan (not shown) disposes the moist air, as shown by arrow 35.

An average fabric load of approximately 4 pounds can be dried in approximately 15 to 18 minutes during the microwave heating cycle. The drying sub-cycle is approximately 50% or more of the microwave heating cycle. The remaining portion of the microwave heating cycle comprises a sanitization sub-cycle which ranges from approximately one-third to one-half of the microwave heating cycle (between 5 to 9 minutes).

During the sanitization sub-cycle, gate 37 is opened, such that there is no airflow 32 through drum 11 and chamber 9. Airflow 29 is continuous throughout the heating cycle, but is caused to exit (arrow 36) through outlet 41 of ducts 26 by means of gate 37, which is caused to be opened about hinge 38.

In the drying sub-cycle, gate 37 is kept shut, so that all of the airflow 29 is directed into chamber 9 via inlet 30.

Airflow 32 passes through drum 11 by means of perforations (not shown) on distal ends 39 of drum 11.

Whether airflow 29 is directed into chamber 9 via inlet 30, or is caused to exit outlet 41, air is continuously passed over magnetrons 31 in order to cool them.

During the sanitization sub-cycle, when inlet 30 is closed to the airflow 29, evaporated moisture from the wet fabric in drum 11 is caused to accumulate and become heated within chamber 9.

It is the heated effluent in combination with the microwave field effect which has been shown to sanitize the fabrics.

The sanitization experiments tested fabric impregnated with many different bacterial strains, some of which includes: *E. Coli;* Salmonella; Shigella and *P. aeruginosa,* etc.

The heated, accumulated effluent emanating from the fabrics was allowed to reach a maximum temperature of approximately 60° C. Higher temperatures may be reached for short periods of time without harming the fabric, analogous to a pasturization technique.

In the many tests which were conducted, many bacterial strains were found to be non-viable after 72 hours of incubation on an appropriate medium after removal from the drum 11.

Generally speaking, the sanitization sub-cycle is conducted at the beginning portion of the microwave heating cycle, and then the remainder of the cycle is substantially comprises of the drying sub-cycle.

It is also contemplated, that a second sanitization sub-cycle of approximately 0.5 to 1.5 minutes in duration can be performed at the very end of the drying sub-cycle. This second sanitization sub-cycle may be necessary where air-borne contaminants may be excessive, or where the fabric is excessively loaded with virulent strains of bacteria.

However, where airflow 32 is filtered prior to entering chamber 9, or where the inlet air is fairly clean, the need for a second sanitization sub-cycle may be unnecessary. For this purpose, a filter may be provided at inlet 30 and/or in ducts 26.

Having thus described this invention, what is desired to be protected by Letters Patent is presented by the subsequently appended claims.

What is claimed is:

1. A method of sanitizing articles by microwave irradiation, comprising the steps of:
   (a) heating articles by microwaves in a sealed heating chamber containing heated water vapor below the boiling point; and
   (b) causing said heated water vapor to accumulate and become further heated below the boiling point within said sealed chamber, whereby said articles will be sanitized by the combination of the microwave field effect and said heated water vapor.

* * * * *